US00PP23248P2

(12) United States Plant Patent
Snoeijer

(10) Patent No.: US PP23,248 P2
(45) Date of Patent: Dec. 11, 2012

(54) ***CLEMATIS* PLANT NAMED 'ZOANG'**

(50) Latin Name: ***Clematis* hybrid**
Varietal Denomination: Zoang

(76) Inventor: Wim Snoeijer, Gouda (NL)

( * ) Notice: Subject to any disclaimer, the term of this patent is extended or adjusted under 35 U.S.C. 154(b) by 80 days.

(21) Appl. No.: 12/932,026

(22) Filed: Feb. 16, 2011

(51) Int. Cl.
*A01H 5/00* (2006.01)

(52) U.S. Cl. ..... Plt./228
(58) Field of Classification Search ..... Plt./228
See application file for complete search history.

*Primary Examiner* — June Hwu
(74) *Attorney, Agent, or Firm* — Penny J. Aguirre

(57) ABSTRACT

A new cultivar of *Clematis* named 'Zoang', characterized by its free-flowering habit with flowers that are a strong red-purple color in spring and almost white with a strong red-purple stripe in summer with little fading, it climbing plant habit, and its cold hardiness to at least U.S.D.A. Zone 6.

2 Drawing Sheets

Botanical classification: *Clematis* hybrid.
Variety denomination: 'Zoang'.

BACKGROUND OF THE INVENTION

The present invention relates to a new and distinct cultivar of *Clematis* if hybrid origin (Patens Group) and will be referred to hereafter by its cultivar name 'Zoang'. 'Zoang' is grown as an herbaceous climbing plant for use in the landscape or as a flowering potted plant for the terrace.

'Zoang' derived from an ongoing breeding program by the inventor in his nursery in Boskoop, The Netherlands. The goal of the selection was to select a hardy climber with uniquely colored flowers that could be grown for different purposes in the garden. 'Zoang' was selected in 2003 and arose from a controlled cross made in 1999 between the female parent, *Clematis* 'Mrs. George Jackman' (not patented) and the male parent, *Clematis* 'Andromeda' (not patented).

Asexual reproduction of the new cultivar was first accomplished by internodial stem cuttings under the direction of the inventor in Boskoop, The Netherlands in 2003. The characteristics of this cultivar have been determined to be stable and are reproduced true to type in successive generations.

SUMMARY OF THE INVENTION

The following traits have been repeatedly observed and represent the characteristics of the new cultivar as grown outdoors and observed for five years in Boskoop, The Netherlands. These attributes in combination distinguish 'Zoang' from other cultivars of *Clematis* known to the inventor.

1. 'Zoang' exhibits upright flowers that are deep red-purple in color in spring and becoming near white with a red-purple stripe in summer.
2. 'Zoang' blooms in spring and even more abundantly in summer.
3. 'Zoang' has flowers with a very strong tepal color that fades very little.
4. 'Zoang' exhibits a climbing growth habit.
5. 'Zoang' is cold hardy to at least U.S.D.A. Zone 6.

'Zoang' differs from its female parent, 'Mrs. George Jackman', in having flowers that are striped with a red-purple color rather than white. 'Zoang' differs from its male parent, 'Andromeda', in having flowers that are heavily striped with red-purple rather than white flowers with a small amount of red-purple stripes. 'Zoang' can be most closely compared to the cultivars 'Nelly Moser' (not patented) and 'Dr. Ruppel' (not patented). 'Nelly Moser' differs from 'Zoang' in having larger flowers that are less abundant in the second flush and stamens and pistils that are red in color. 'Dr. Ruppel' differs from 'Zoang' in having larger flowers and tepals that are orchid-purple with red-purple centers rather than white with red-purple centers.

BRIEF DESCRIPTION OF THE DRAWING

The accompanying colored photographs illustrate the overall appearance and distinct characteristics of the new *Clematis*. The photographs were taken of three year-old plants of 'Zoang' as grown in one-gallon containers in Boskoop, The Netherlands.

The photograph in FIG. 1 shows the habit in bloom in the summer.

Figure 1:
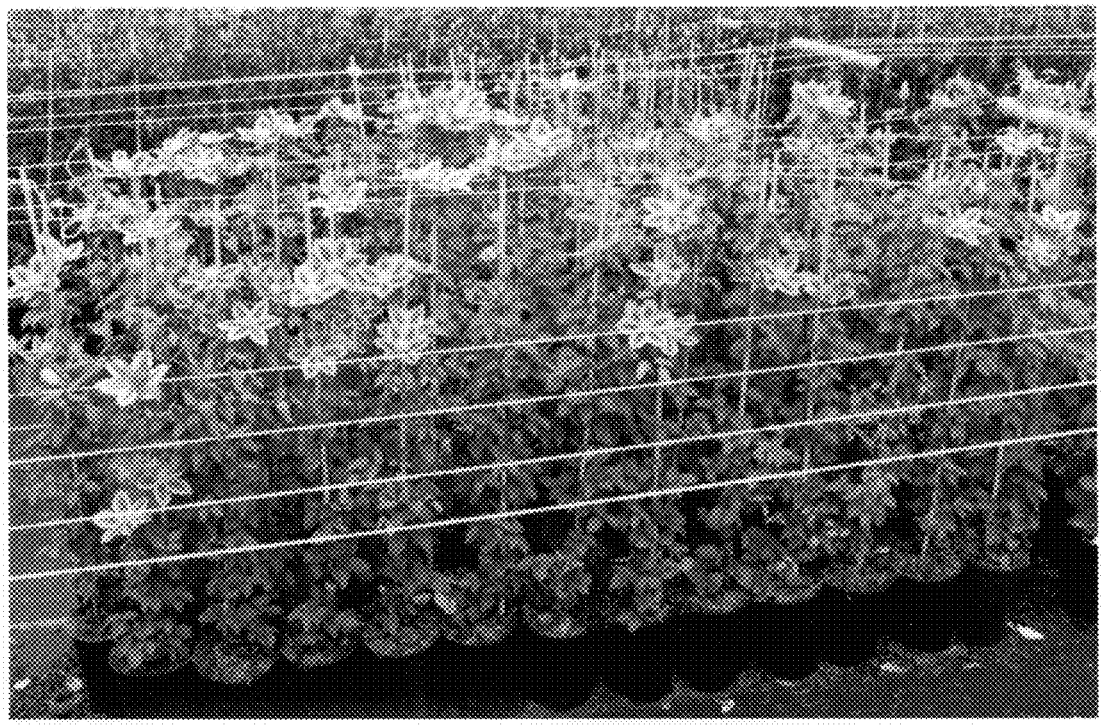
Figure 2:
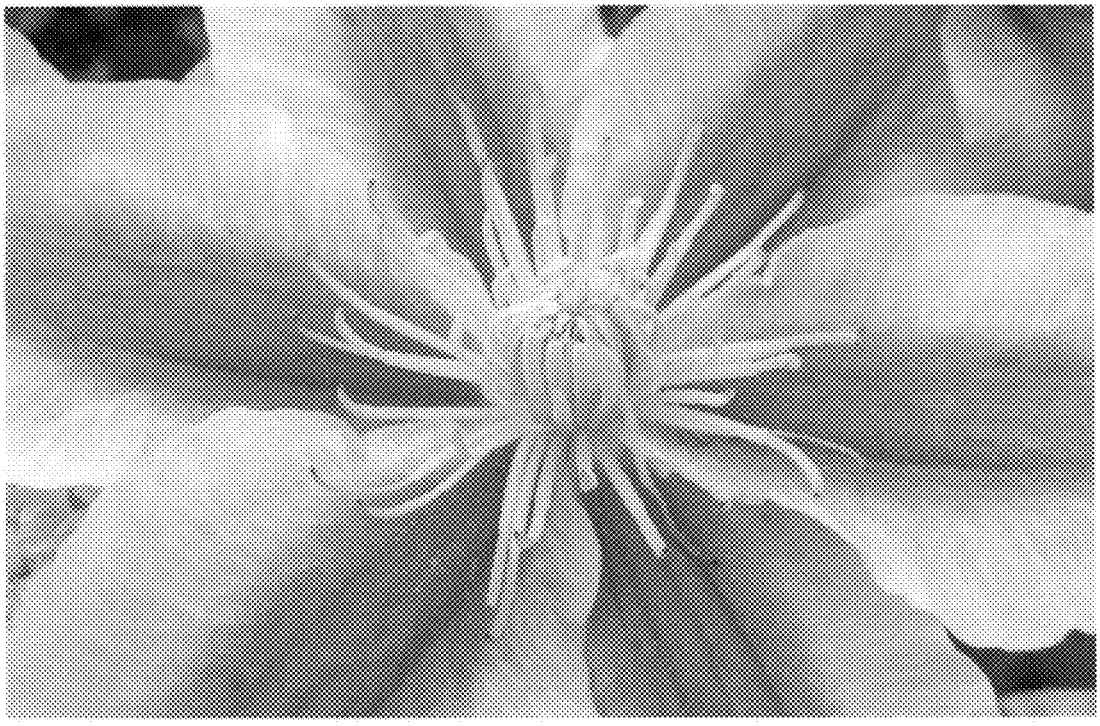

The photograph in FIG. 2 shows the stamens and pistil in a summer flower.

Figure 3:
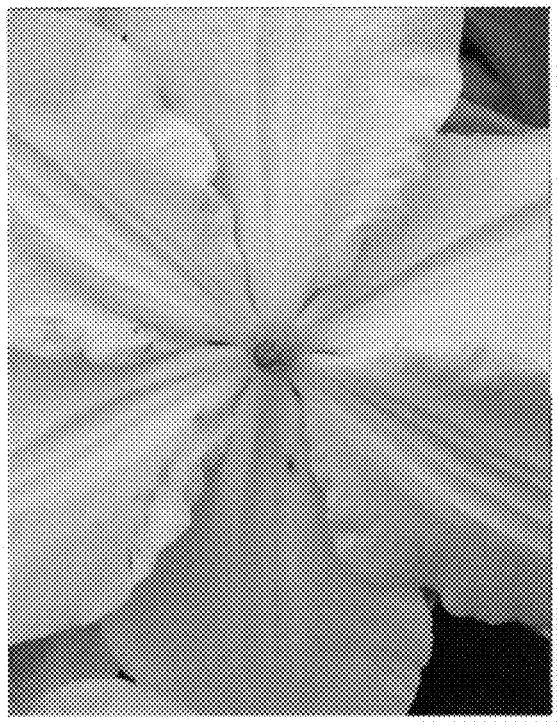

The photograph in FIG. 3 shows the back of the flower.

Figure 4:
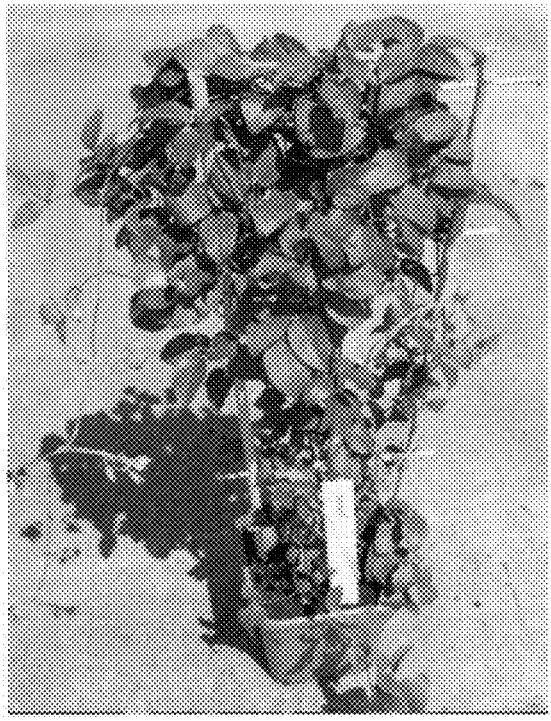

The photograph in FIG. 4 shows a growing plant.

Figure 5:
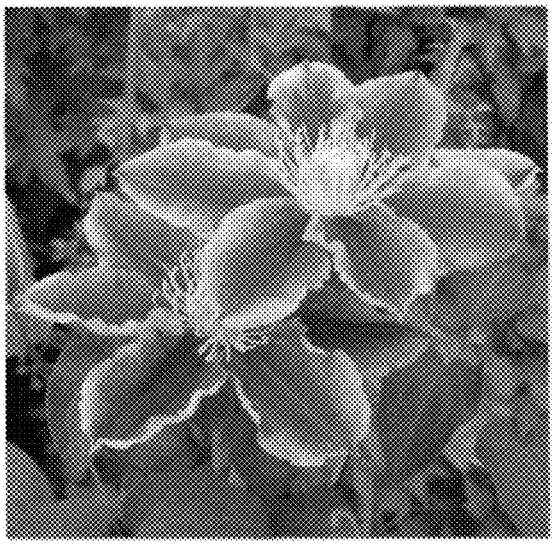

The photograph in FIG. 5 shows spring flowers.

Figure 6:
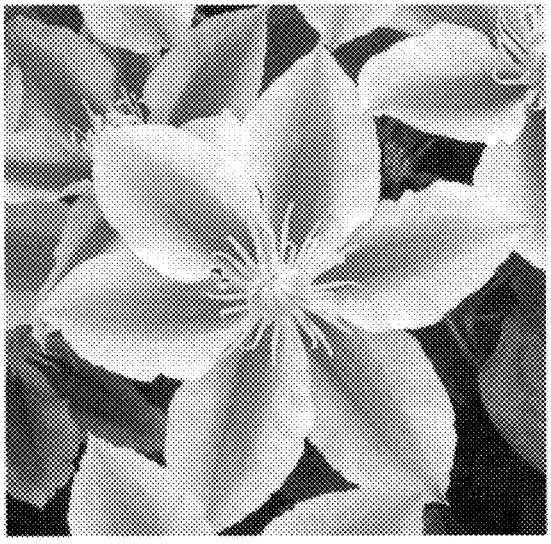

The photograph in FIG. 6 shows summer flowers.

The colors in the photographs are as close as possible with the digital photography techniques available, the color values cited in the detailed botanical description accurately describe the colors of the new *Clematis*.

DETAILED BOTANICAL DESCRIPTION

The following is a detailed description of three year-old plants of 'Zoang' as grown outdoors in one-gallon containers under full sun at a nursery in Boskoop, The Netherlands. The phenotype of the new cultivar may vary with variations in environmental, climatic, and cultural conditions, as it has not been tested under all possible environmental conditions. The color determination is in accordance with The 2001 R.H.S.

Colour Chart of The Royal Horticultural Society, London, England, except where general color terms of ordinary dictionary significance are used.

General description:

*Botanical classification.*—*Clematis* 'Zoang' (classified in the Patens Group).

*Blooming period.*—Blooms for 4 to 6 weeks in spring and more abundantly in summer for 6 to 8 weeks.

*Plant habit.*—Herbaceous climber.

*Height and spread.*—Three year-old plant is about 15 cm at base with a height of about 2 m when pruned after first flowering.

*Cold hardiness.*—At least to U.S.D.A. Zone 6.

*Culture.*—Moist but well-drained soils in full sun with roots shaded.

*Diseases.*—No resistance to wilt has been observed.

*Root description.*—Fleshy.

Growth and propagation:

*Propagation.*—Internodial softwood cuttings from vegetative shoots.

*Root initiation.*—Roots develop in 6 weeks in summer under greenhouse conditions.

*Time required for root development.*—75 to 90 days to develop a 5-cm container from a cutting 5 cm in length.

*Growth rate.*—Moderately vigorous once planted in the landscape.

Stem description:

*Shape.*—Round and 6 ribbed.

*Stem color.*—166A.

*Stem size.*—About 2 m (including peduncle and terminal pedicel) in length, an average of 4 mm in diameter.

*Stem surface.*—Sparsely hairy with short hairs and more densely near the nodes.

*Internode length.*—Ranges from 3 to 9 cm.

*Branching.*—Basal branching.

Foliage description:

*Leaf arrangement.*—Opposite.

*Leaf division.*—Ternate.

*Leaf size.*—Average of 10 cm in length and width.

*Leaflet shape.*—Ovate.

*Leaflet base.*—Obtuse to oblique.

*Leaflet apex.*—Acute.

*Leaflet fragrance.*—None.

*Leaflet venation.*—Slightly reticulate.

*Leaflet margins.*—Entire.

*Leaflet attachment.*—Petioluled with leaf petioled, 1 to 7 cm in length, round in shape, 166A in color, curled, surface is sparse covered with hairs.

*Leaflet surface.*—Glabrous on both surfaces.

*Leaflet size.*—Up to 5 cm in length and 3 cm in width.

*Leaflet color.*—Upper surface 139A, lower surface 147C.

*Petioles and petiolules.*—Petiole; average of 4.5 cm in length, 166A in color, round, surface with a few scattered hairs, petiolule; average of 1 cm in length, 166A in color, round, surface with a few scattered hairs.

Inflorescence description:

*Inflorescence type.*—Solitary.

*Inflorescence arrangement.*—Terminal and axillary on young shoots.

*Peduncles.*—2 to 8 cm in length, 143C in color, surface sparsely covered with short hairs at nodes.

*Peduncle bracts.*—Leaf-like, division simple, about 4 cm in length and 3 cm in width, color and surface is the same as leaflets.

*Bud description.*—Held upright, ovate in shape, about 4 cm in length and 1.5 cm in width, 139B in color with seams NN155 in color.

*Flower fragrance.*—None.

*Lastingness of flowers.*—Individual flowers last about 7 days, the tepals are caducous followed by the stamens.

*Flower quantity.*—Solitary flowers, terminal and axillary on young shoots, on a 3 year old plant about 20 to 30 flowers in spring and 50 to 70 flowers in summer.

*Flower type.*—Single, open to nearly horizontal, spring flowers in a round shape, summer flowers more star shaped.

*Flower aspect.*—Upright facing.

*Flower size.*—Range from 10 cm in diameter and about 7 cm in depth.

*Tepal number.*—Spring flowers about 8, summer flowers about 6.

*Tepal shape.*—Broadly elliptic.

*Tepal apex.*—Acuminate.

*Tepal base.*—Cuneate.

*Tepal arrangement.*—Un-fused and overlapping at base.

*Tepal margins.*—Entire, opening a bit wavy but quickly smooth.

*Tepal surface.*—Upper surface; glabrous, lower surface; margin slightly covered with very short tomentose hairs, more densely tomentose in middle of tepal and decreasing towards base.

*Tepal color.*—Spring flowers upper surface; 71B in center blending to NN155C on margins and base N155C, summer flowers upper surface; 71B blended with 73A in center and base and margins NN155C, spring and summer flowers lower surface; NN155C and slightly suffused with 77C.

*Tepal size.*—Up to 6.6 cm in length and 3.5 cm in width.

Reproductive organs:

*Gynoecium.*—Numerous pistils (about 50), 1 cm in length, style is 158D in color and plumose, stigma is 158A in color, ovary is 143C in color with a hairy surface.

*Androcoecium.*—About 25, filaments are 0.5 to 12 cm in length and 1 mm in width, glabrous surface, and about 158D in color, anthers are 5 mm in length, linear in shape, connective is 2C in color, obtuse and glabrous.

*Seed.*—Seeds are rarely formed and not available for data collection.

It is claimed:

1. A new and distinct cultivar of *Clematis* plant named 'Zoang' as herein illustrated and described.

* * * * *